(12) United States Patent
Li et al.

(10) Patent No.: US 10,404,229 B2
(45) Date of Patent: Sep. 3, 2019

(54) EMI REDUCTION WITHIN A CONNECTOR USING A FEED-THROUGH CAPACITOR

(71) Applicant: CommScope Technologies LLC, Hickory, NC (US)

(72) Inventors: Shi Man Li, Mooresville, NC (US); Chi Tsung Yang, Taoyuan (TW); Chien Chung Lee, New Taipei (TW)

(73) Assignee: CommScope Technologies LLC, Hickory, NC (US)

( * ) Notice: Subject to any disclaimer, the term of this patent is extended or adjusted under 35 U.S.C. 154(b) by 145 days.

(21) Appl. No.: 15/638,877

(22) Filed: Jun. 30, 2017

(65) Prior Publication Data
US 2018/0013245 A1    Jan. 11, 2018

Related U.S. Application Data

(60) Provisional application No. 62/359,958, filed on Jul. 8, 2016.

(51) Int. Cl.
*H03H 1/00* (2006.01)
*H01R 24/00* (2011.01)
(Continued)

(52) U.S. Cl.
CPC ......... *H03H 1/0007* (2013.01); *A61N 1/3754* (2013.01); *H01G 4/35* (2013.01);
(Continued)

(58) Field of Classification Search
CPC ......... H03H 1/0007; H03H 2001/0042; H01R 24/00; H01R 13/7195
(Continued)

(56) References Cited

U.S. PATENT DOCUMENTS 2,911,333 A    11/1959   Capen et al.
3,391,356 A    7/1968   Bolljahn et al.
(Continued)

FOREIGN PATENT DOCUMENTS

CN    2899175 Y    5/2007
CN    202050495 U    11/2011

OTHER PUBLICATIONS

English translation of CN202050495 (Year: 2011).*

*Primary Examiner* — Rakesh B Patel
(74) *Attorney, Agent, or Firm* — Muncy, Geissler, Olds & Lowe, P.C.

(57) ABSTRACT

An EMI filtering, coaxial power connector may be formed as an inline component or a port of a device. The connector may have dimensions to accept F-type coaxial connectors. The connector includes a conductive outer shell with a first opening and a second opening. A dielectric member is disposed within the shell. A conductive pin is supported by the dielectric member. A feed-through capacitor has a central opening and a first lead formed within the central opening. The pin is electrically connected to the first lead. A second lead of the capacitor is formed at an outer perimeter of the capacitor and is electrically connected to the shell. A metal plate is mounted within the shell. The plate is disk-shaped with a central hole. An outer perimeter of the plate is in electrical contact with the shell. The pin passes through the central hole without making electrical contact with the plate, and the plate resides between the second opening of the shell and the capacitor.

20 Claims, 14 Drawing Sheets

(51) Int. Cl.
  *H01R 13/719*   (2011.01)
  *A61N 1/375*    (2006.01)
  *H01G 4/35*     (2006.01)
  *H01R 13/7195*  (2011.01)
  *H01R 13/658*   (2011.01)
  *H01R 24/42*    (2011.01)
  *H01R 13/52*    (2006.01)
  *H01R 13/66*    (2006.01)
  *H01R 24/52*    (2011.01)
  *H01R 24/54*    (2011.01)

(52) U.S. Cl.
  CPC ......... *H01R 13/658* (2013.01); *H01R 13/719* (2013.01); *H01R 13/7195* (2013.01); *H01R 24/00* (2013.01); *H01R 24/42* (2013.01); *H01R 13/5216* (2013.01); *H01R 13/6625* (2013.01); *H01R 24/52* (2013.01); *H01R 24/542* (2013.01)

(58) Field of Classification Search
  USPC .......................................................... 333/182
  See application file for complete search history.

(56) References Cited

U.S. PATENT DOCUMENTS

| | | |
|---|---|---|
| 4,187,481 A | 2/1980 | Boutros |
| 4,563,659 A * | 1/1986 | Sakamoto ............ H03H 1/0007 333/181 |
| 4,846,732 A | 7/1989 | Meelhuysen |
| 5,213,522 A | 5/1993 | Kojima |
| 5,340,325 A | 8/1994 | Pai |
| 5,389,903 A | 2/1995 | Piirainen |
| 5,413,504 A | 5/1995 | Kloecker et al. |
| 5,461,351 A | 10/1995 | Shusterman |
| 5,825,608 A | 10/1998 | Duva et al. |
| 6,152,743 A | 11/2000 | Fox |
| 6,165,019 A | 12/2000 | Kha et al. |
| 6,888,715 B2 | 5/2005 | Stevenson et al. |
| 7,632,122 B2 | 12/2009 | Pesant |
| 8,858,262 B2 | 10/2014 | Daughtry, Jr. et al. |

* cited by examiner

EMI REDUCTION WITHIN A CONNECTOR USING A FEED-THROUGH CAPACITOR

This application claims the benefit of U.S. Provisional Application No. 62/359,958, filed Jul. 8, 2016, which is herein incorporated by reference.

BACKGROUND OF THE INVENTION

1. Field of the Invention

The present invention relates to a coaxial connector for supplying power to a device. More particularly, the present invention relates to a coaxial connector, which includes EMI filtering and shielding features to reduce the likelihood of EMI entering the device via the power connection, so as to reduce the likelihood of EMI interference with the communication frequencies utilized within the device.

2. Description of the Related Art

It is generally known in the existing arts, that a device which operates on communication signals of high frequencies, such as splitters, amplifiers and other devices in a home-subscriber data system, e.g., VoIP, Internet, CATV system, may receive power over a coaxial cable. The coaxial cable is terminated to an F-type connector and screwed, or pushed, onto a power port of the device. The device is usually housed inside of a metal enclosure to provide shielding to prevent electro-magnetic interference (EMI) from entering the device and/or prevent the radio frequency signal within the device from escaping the device and becoming EMI to a neighboring device.

Sometimes the coaxial power cable can act as an antenna to pick up EMI from outside sources, such as cellular phone signals, WiFi signals, cordless phone signals, HAM/CB radio signals, over the air TV signals, etc. The EMI can travel down the coaxial power cable and into the power port of the device. In other words, the power port can be a weak-link in the overall EMI shielding of the device, as the port is an opening in the otherwise substantially-sealed metal enclosure of the device. Also, the radio frequencies, utilized within the device, may escape the shielding of the device's house via the opening of the power port and then radiate down the coaxial power cable to cause EMI interference for neighboring devices.

One attempt in the prior art to prevent EMI from entering and exiting the conductors associated with a power port of a shielded device can be seen in U.S. Pat. No. 7,632,122, which is herein incorporated by reference. U.S. Pat. No. 7,632,122 notes that prior art devices have included an EMI filtering section on the printed circuit board (PCB) to remove EMI from the power signal line just as it enters the PCB. See col. 1, lines 39-14. U.S. Pat. No. 7,632,122 has as an objective to remove components from the crowded PCB, and the invention of U.S. Pat. No. 7,632,122 places a small circular PCB within the port connector of the device itself. U.S. Pat. No. 7,632,122 also notes that prior art devices have included an EMI filtering device as a separate inline filter. U.S. Pat. No. 7,632,122 speaks negatively of separate inline filters, which add components and costs to the overall system, and instead recommends including a separate PCB within the power input port itself. See col. 1, lines 39-55.

SUMMARY OF THE INVENTION

The Applicant has appreciated some drawbacks in the background art. The PCB 18 within the power port of U.S. Pat. No. 7,632,122 has at least a center conductive pad 29 with a central opening 36, a non-conductive material 39b that surrounds the center conductive pad 29, a ground plane 19 surrounding the non-conductive material 39b, non-conductive circumferential material 39a surrounding the ground plane 19, and at least one capacitor 20 electrically connecting the conductive pad 29 and the ground plane 19. See col. 5, lines 23-30. During assembly the ground plane 19 is soldered to the connector's outer shell, the center pin of the conductor is soldered to the conductive pad 29 and the one or more capacitors 20 are soldered to the conductive pad 29 and the ground plane 19. See col. 6, lines 6-14.

The PCB 18 of U.S. Pat. No. 7,632,122 is relatively complex and requires several additional assembly steps, as compared to the present invention. It is an object of the present invention to provide an EMI shielding structure which is simpler in design, requires fewer parts, requires fewer solder processes and/or is easier to assemble. In one embodiment of the present invention, no PCB within the power port is required. Further, one embodiment of the present invention provides improved weather resistance to prevent corrosion and potential damage to the EMI filter. Also, it is believed that the design of the present invention provides improved EMI shielding and is suitable for an inline filter as a separate component part.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limits of the present invention, and wherein.

DETAILED DESCRIPTION OF EMBODIMENTS OF THE INVENTION

Figure 1:
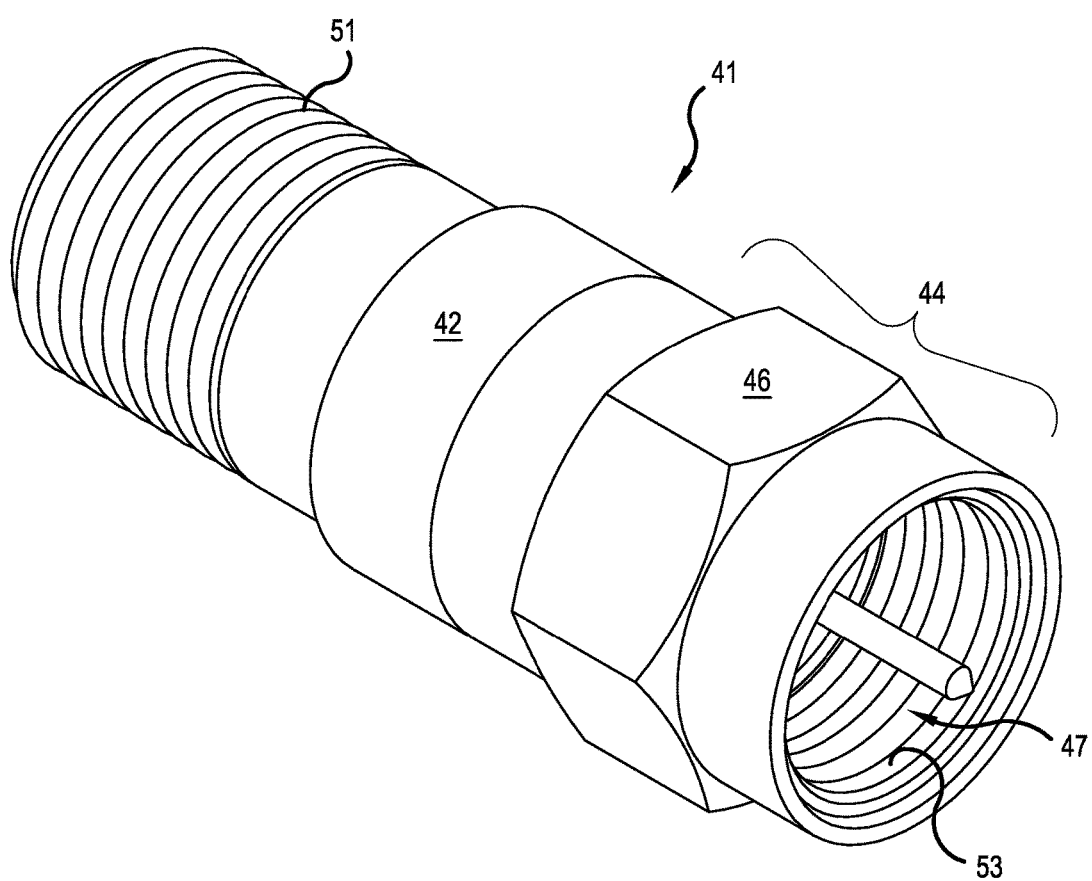
FIG. 1 is a front perspective view of an EMI filtering, coaxial, power connector for use as an inline filter, in accordance with the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "lateral", "left", "right" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. The device may be otherwise oriented (rotated 90 degrees or at other orientations) and the descriptors of relative spatial relationships used herein interpreted accordingly.

Figure 2:
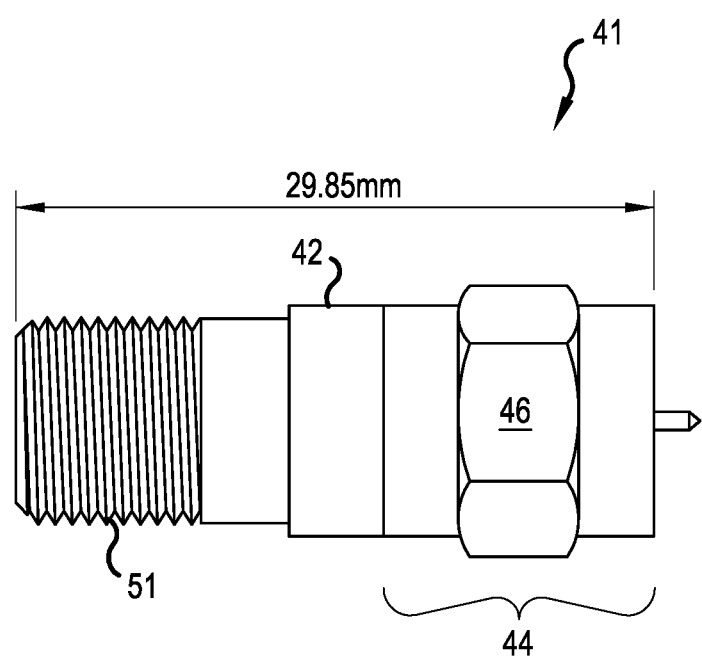
FIG. 2 is a side view of the connector of FIG. 1.
Figure 3:
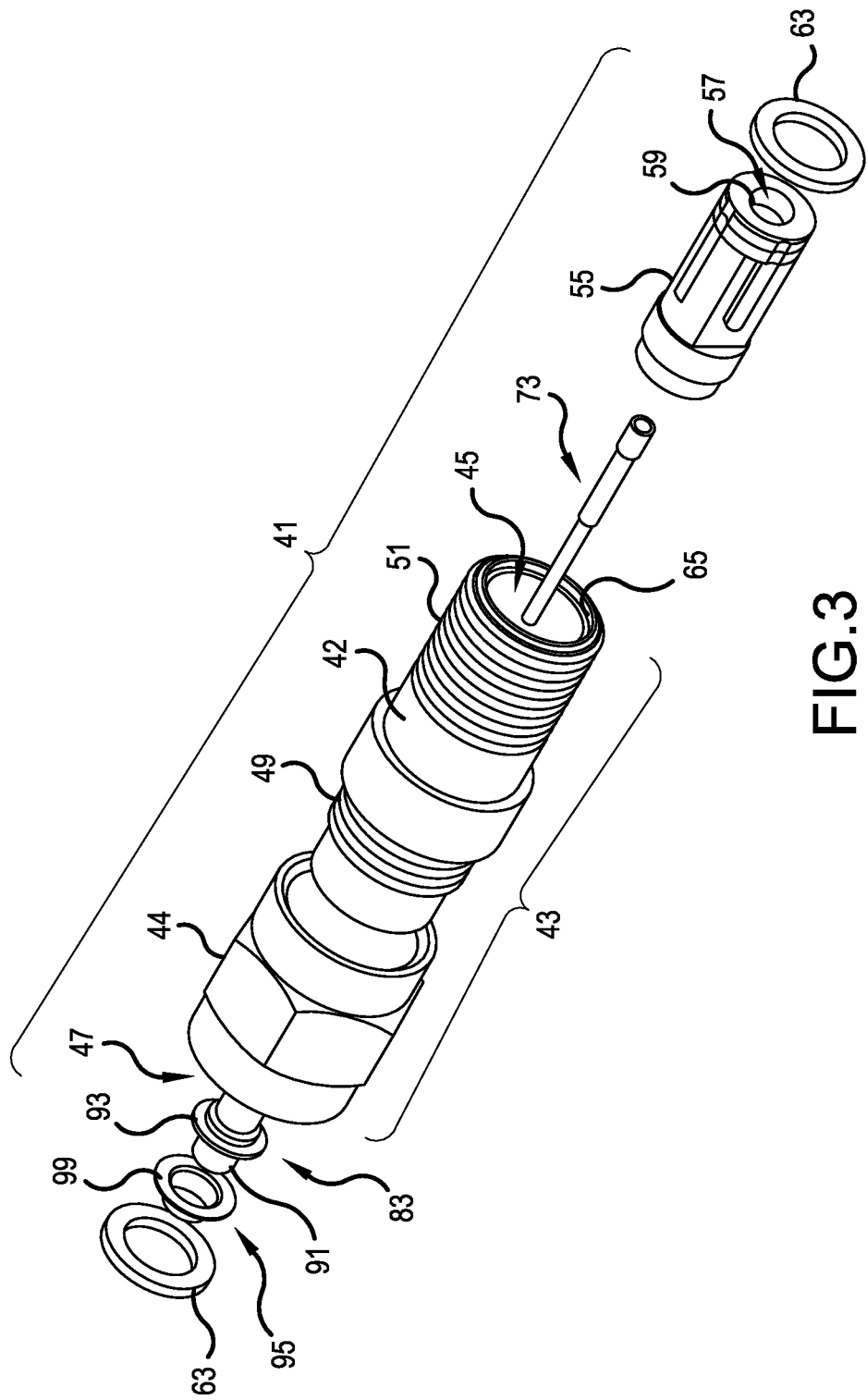
FIG. 3 is rear perspective view of the connector of FIGS. 1 and 2, in an exploded state to illustrate the various components therein.

FIGS. 1 and 2 are a front perspective view and a side view of an EMI filtering, coaxial, power connector 41 for use as an inline filter, in accordance with the present invention. FIG. 3 is rear perspective view of the connector 41 of FIGS. 1 and 2, in an exploded state to illustrate the various parts therein.

Figure 4:
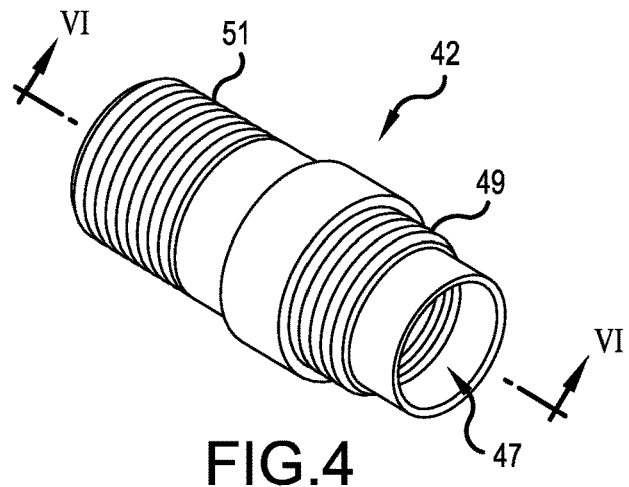
FIG. 4 is a front perspective view of a body of a conductive outer shell of the connector of FIGS. 1-3.
Figure 5:
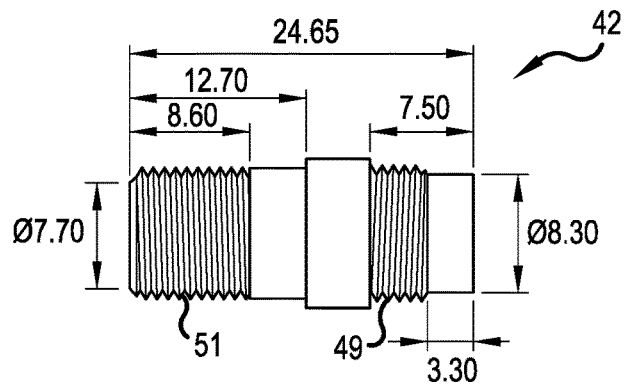
FIG. 5 is a side view of the body of FIG. 4.
Figure 6:
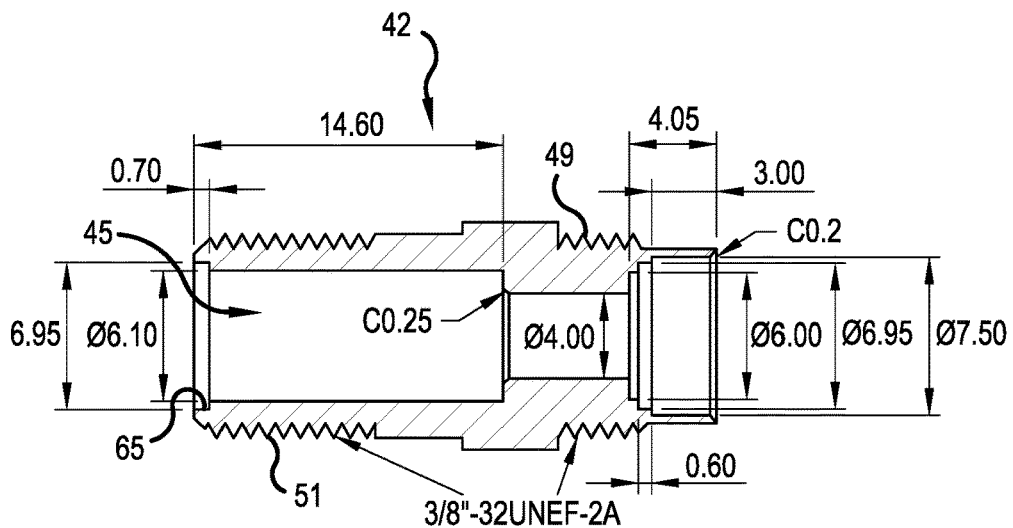
FIG. 6 is a cross sectional view taken through line VI--VI in FIG. 4.

The connector 41 includes, as its largest component part, a conductive outer shell 43 with a first opening 45 and a second opening 47. In a preferred embodiment of the connector 41, the conductive outer shell 43 is formed of two metal pieces, namely a body 42 and a male cap 44. FIG. 4 is a front perspective of the body 42. FIG. 5 is a side view of the body 42. FIG. 6 is a cross sectional view taken through line VI--VI in FIG. 4. The general dimensions of the body 42 are shown in FIGS. 5 and 6 and are given in millimeters. However, it is to be understood that the dimensions are shown for only one of the preferred embodiments, and that other dimensions are within the purview of the present invention.

Figure 7:
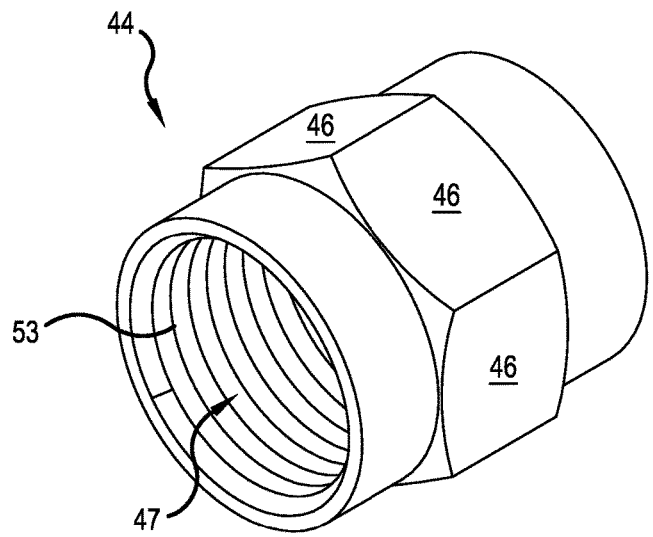
FIG. 7 is a front perspective view of a male cap of the connector of FIGS. 1-3.
Figure 8:
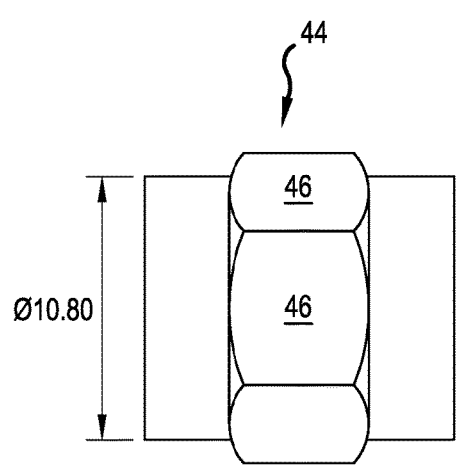
FIG. 8 is a side view of the male cap of FIG. 7.
Figure 9:
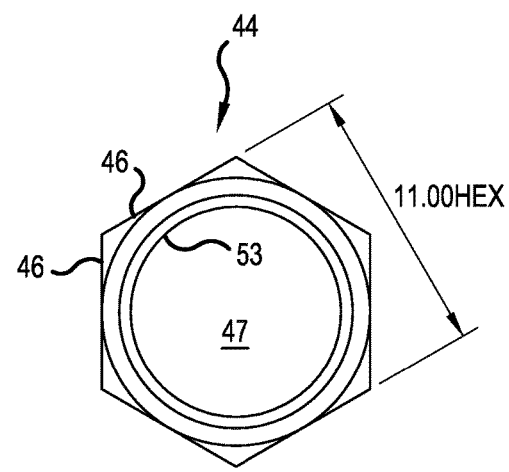
FIG. 9 is a front view of the male cap of FIGS. 7 and 8.

FIG. 7 is a front perspective view of the male cap 44. FIG. 8 is a side view of the male cap 44. FIG. 9 is a front view of the male cap 44. The male cap 44 is captured by tracks 49 formed on an outer surface of the body 42 and can rotate about the body 42 via the tracks 49. The male cap 44 includes inner threads 53 formed around an inner surface surrounding the second opening 47 of the conductive outer shell 43 to engage another female coaxial connector. An outer surface surrounding the first opening 45 of the body 42 includes first threads 51 for engaging inner threads 53 of another male coaxial connector. The outside structural features of the conductive outer shell 43 of the inline connector 41 may be formed like other inline filters, e.g., notch filters as previously used in the CATV art to restrict pay channels.

For example, hexagonal tool surfaces 46 may be formed on the outer surface, with an eleven millimeter (11 mm) distance existing between the parallel flats of the hexagonal tool surfaces 46.

Figure 10:
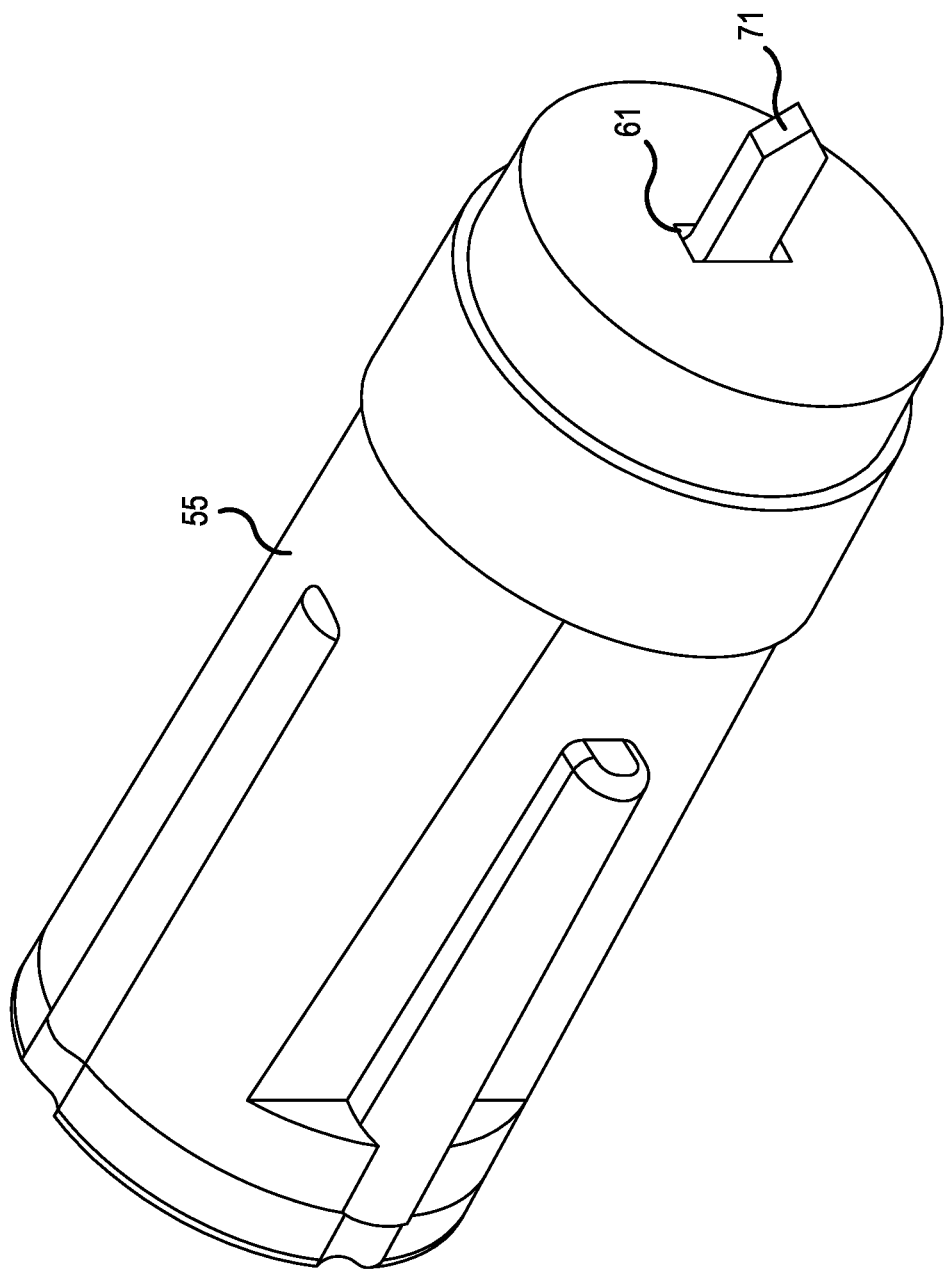
FIG. 10 is a front perspective view of a dielectric member of the connector of FIGS. 1-3.

FIG. 10 is a front perspective view of a dielectric member 55. The dielectric member 55 is disposed within the conductive outer shell 43. The dielectric member 55 has a channel 57 formed therein with a third opening 59 and a fourth opening 61. The dielectric member 55 may be inserted into the first opening 45 of the conductive outer shell 43 and attached therein by a snap fit or adhesive, e.g., epoxy. Alternatively, a dielectric or metal ring 63 may be press fitted, punch riveted and/or adhered into an inset groove ring 65 at the first opening 45 of the conductive outer shell 43 to abut and hold the dielectric member 55 inside the conductive outer shell 43, so that the dielectric member 55 may not slide out of the first opening 45 of the conductive outer shell 43.

Inside the dielectric member 55 resides a pin receiving clamp 67. See FIG. 25. The pin receiving clamp 67 is directly attached to the dielectric member 55 via a snap fit and/or epoxy and includes a first end 69 located proximate the first opening 45 of the conductive outer shell 43. The first end 69 of the pin receiving clamp 67 is dimensioned to receive a pin of a male coaxial connector mated to the first opening 45 of the conductive outer shell 43. A second end 71 of the pin receiving clamp 67 is formed as a flat plate and extends out the fourth opening 61 of the dielectric member 55, as best seen in FIG. 10.

Figure 11:
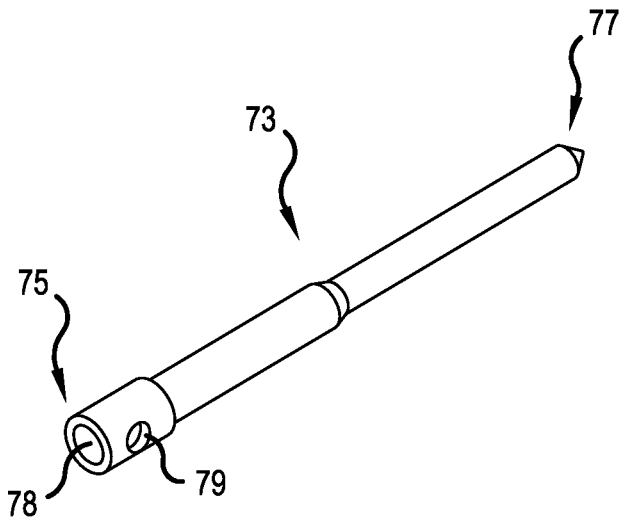
FIG. 11 is a rear perspective view of a conductive pin of the connector of FIGS. 1-3.
Figure 12:
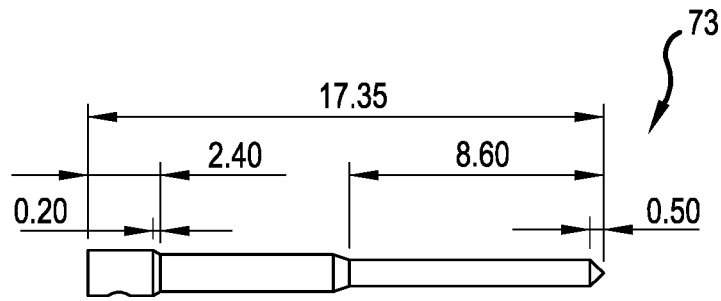
FIG. 12 is top view of the conductive pin of FIG. 11.
Figure 13:
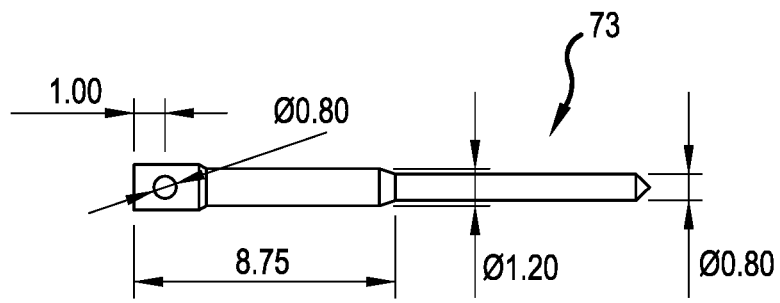
FIG. 13 is a side view of the conductive pin of FIGS. 11 and 12.

The EMI filtering connector 41 further includes a conductive pin 73 having a first end 75 and a second end 77. FIG. 11 is a rear perspective view of the conductive pin 73. FIGS. 12 and 13 are top and side views, respectively, of the conductive pin 73. Illustrative dimensions in millimeters are given in FIGS. 12 and 13 to provide an example of the size of the conductive pin 73, in one preferred embodiment of the present invention.

Figure 14:
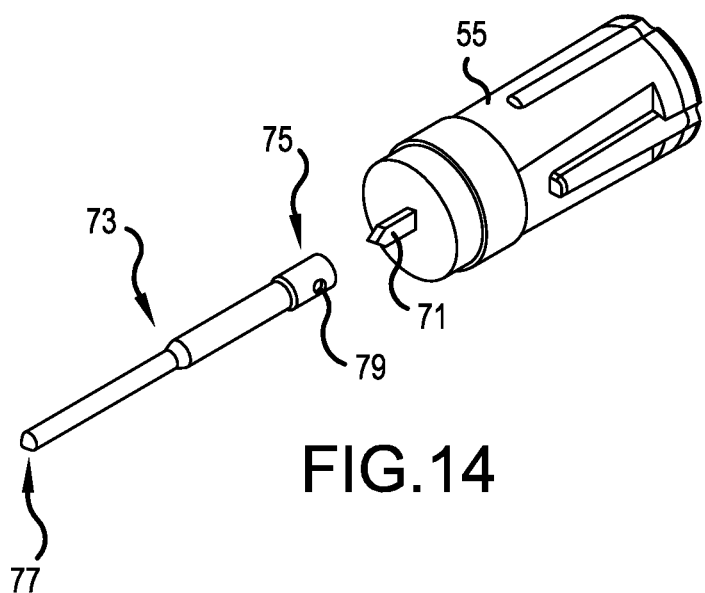
FIG. 14 is a front perspective view of the conductive pin just prior to attachment to an end of a pin clamp, housed within the dielectric member.
Figure 15:
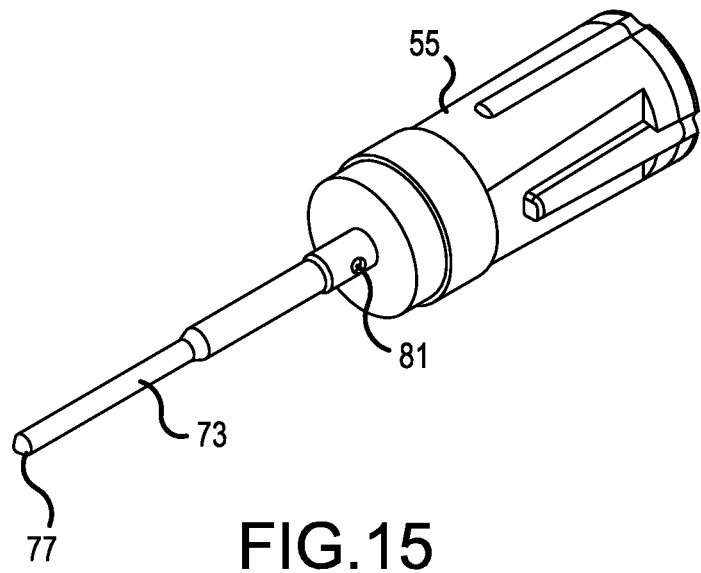
FIG. 15 is a front perspective view of the conductive pin attached to the end of the pin clamp.

As best seen in FIGS. 14 and 15, the conductive pin 73 is attached to the dielectric member 55 by an attachment to the second end 71 of the pin receiving clamp 67. More specifically, the first end of the conductive pin 72 includes a slot 78, and the slot 78 receives the flat plate of the second end 71 of the pin receiving clamp 67. A bore 79 is formed on a side of the conductive pin 73 proximate the first end 75 and opens to the slot 78. Solder 81, or a similar fixing compound such as conductive epoxy, is inserted into the bore 79 to affix and electrically connect the first end 75 of the conductive pin 73 to the second end 71 of the pin receiving clamp 67.

The second end 77 of the conductive pin 73 extends to a point proximate the second opening 47 of the conductive outer shell 43. The second end 77 of the conductive pin 73 acts in conjunction with the inner threads 53 formed proximate the second opening 47 of the conductive outer shell 43 to form a male coaxial connector.

Figure 16:
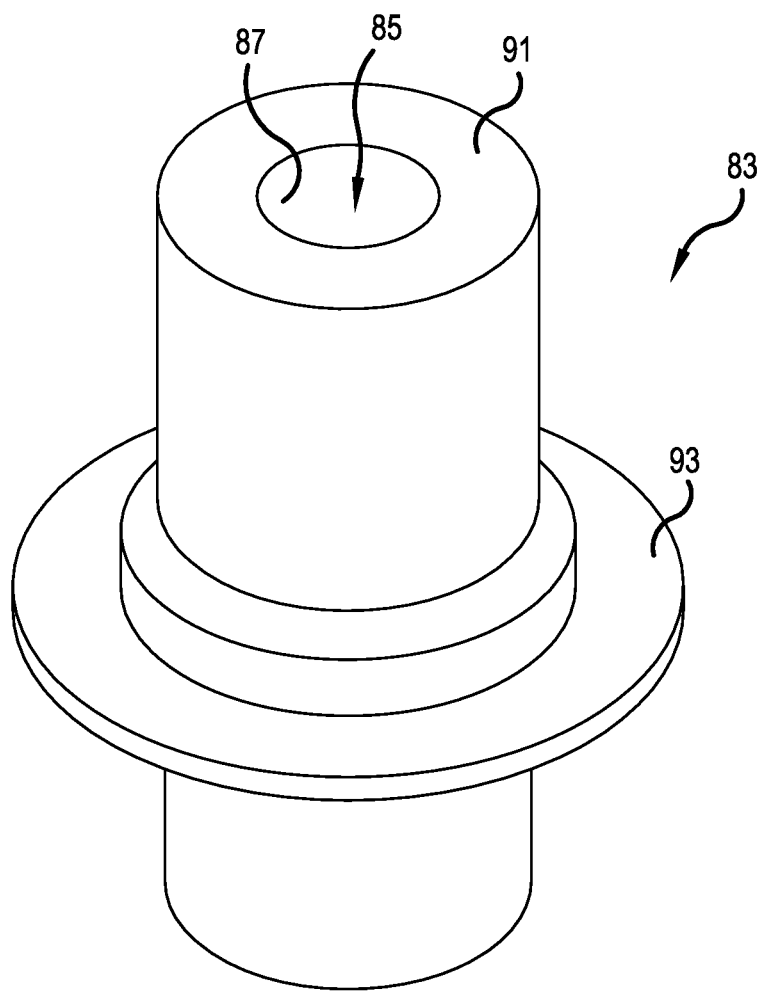
FIG. 16 is a perspective view of a feed-through capacitor of the connector of FIGS. 1-3.
Figure 20:
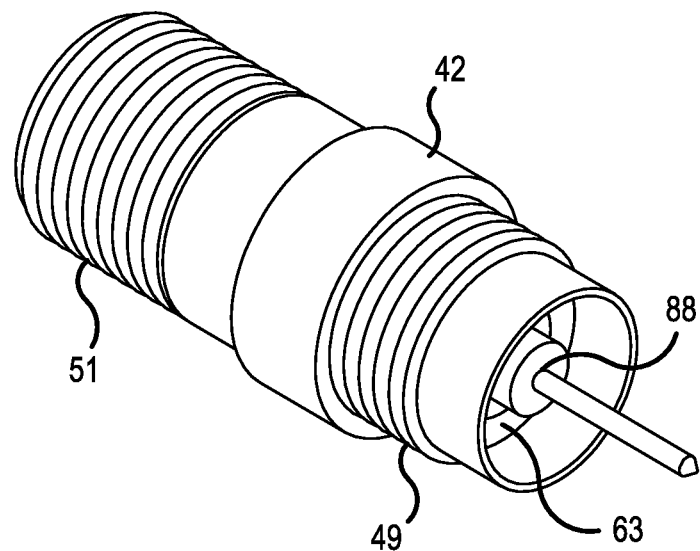
FIG. 20 is a front perspective view of a solder connection between the conductive pin and the feed-through capacitor.

At least one capacitor is mounted within the conductive outer shell 43. In a most preferred embodiment, the at least one capacitor is a feed-through capacitor 83, as shown in FIG. 16. A feed-through capacitor 83 is known in the existing arts, but to the best of Applicant's knowledge has here-to-fore not been employed within a coaxial power connector. The feed-through capacitor 83 has a central opening 85. A first lead 87 of the capacitor is formed within the central opening 85, e.g., a metal inner wall of the central opening 85. The conductive pin 73 passes through the central opening 85 and is electrically connected to the first lead 87. The electrical connection may be formed by solder 88, conductive epoxy or a similar manner. See the perspective view in FIG. 20.

A dielectric material 91 surrounds the first lead 87. A second lead 93 is formed at an outer perimeter of the feed-through capacitor 83. In a preferred embodiment, the second lead 93 is formed entirely around the outer perimeter of the feed-through capacitor 83. The dielectric constant of the dielectric material 91, and the dimensions and positioning of the various components of the feed-through capacitor 83, provide a capacitance of about 1,000 pF between the first and second leads 87 and 93. However, other capacitances are within the scope of the present invention, such as about 200 pF to 4,000 pF, or about 500 pF to 3,000 pF, more preferably about 700 pF to 2,500 pF. The function of the capacitance is to remove EMI frequencies from the power signal being supplied via the F-type connector, and capacitors with greater or less capacitance will be able to accomplish that function. Also, more than one feed-through capacitor may be soldered to the conductive pin 73 to accomplish the function. However, additional capacitors would not be a preferred embodiment, due to the added costs and assembly steps.

Figure 17:
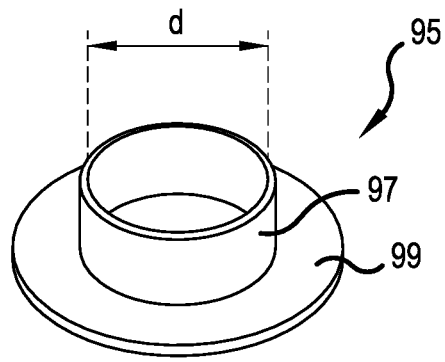
FIG. 17 is a perspective view of a metal plate of the connector of FIGS. 1-3
Figure 18:
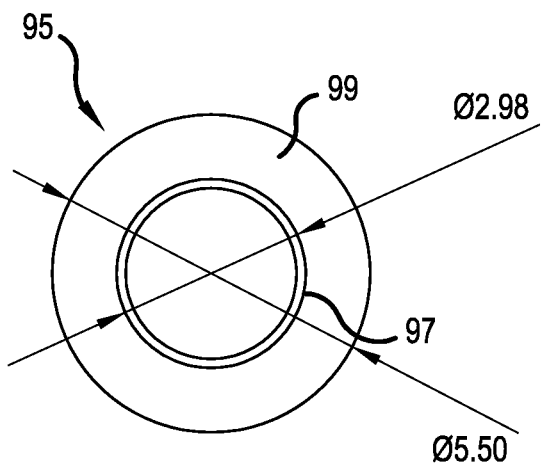
FIG. 18 is a top view of the metal plate of FIG. 17.
Figure 19:
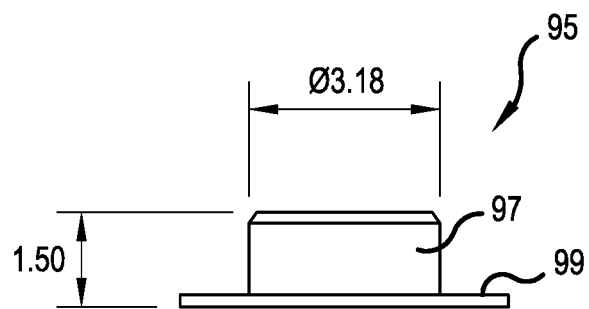
FIG. 19 is a side view of the metal plate of FIGS. 17 and 18.

The second lead 93 is electrically connected to the conductive outer shell 43. To accomplish this, a metal plate 95, as shown in FIGS. 17-19 is employed. FIG. 17 is a perspective view of the metal plate 95. FIGS. 18 and 19 are top and side views, respectively, of the metal plate 95. Illustrative dimensions in millimeters are given in FIGS. 18 and 19 to provide an example of the size of the metal plate 95, in one preferred embodiment of the present invention.

The metal plate 95 includes a cylindrical section 97 with a central hole, having an inner diameter d which closes matches, or is only slightly larger than, the outer diameter of the dielectric material 91 of the feed-through capacitor 83. A rim 99 is disk-shaped and formed integrally with, or attached to, the cylindrical section 97. The metal plate 95 may be formed of brass, nickel plated bronze, aluminum, copper, or other conductive metals or alloys, and may also be formed of a same material as used to construct the conductive outer shell 43.

During assembly, the metal plate 95 is mounted within the conductive outer shell 43. An outer perimeter of the rim 99 of the metal plate 95 is placed into electrical contact with the conductive outer shell 43. For example, the rim 99 may be pressure fitted against, punch riveted in place and/or soldered to a rim within the conductive outer shell 43, so that no gaps are present around the entirety of the outer perimeter of the rim 99 and the conductive outer shell 43. The central hole of the cylindrical portion is passed over the feed-through capacitor 83 until the rim 99 abuts and is in electrical contact with the second lead 93. The rim 99 may be soldered to the second lead 93. In other words, an inner perimeter of the central hole of the cylindrical section 97 of the conductive plate 95 may be soldered to the second lead 93 of said feed-through capacitor around an entirety of the perimeter of the second lead 93, so that no gaps are present.

Figure 22:
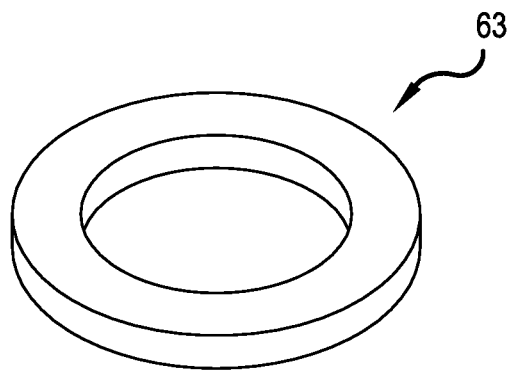
FIG. 22 is a perspective view of a metal ring of the connector of FIGS. 1-3
Figure 23:
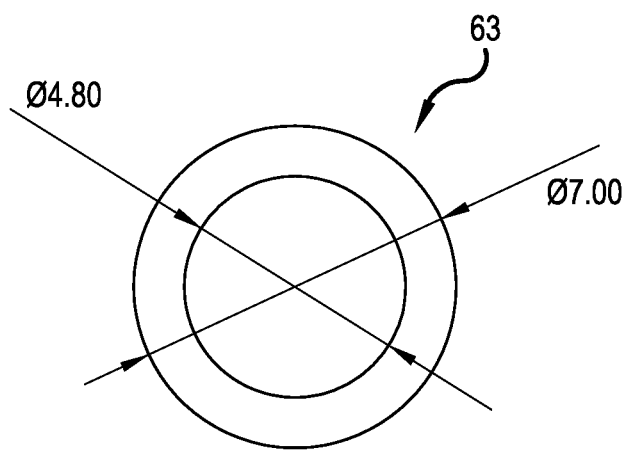
FIG. 23 is a top view of the metal ring of FIG. 22.
Figure 24:
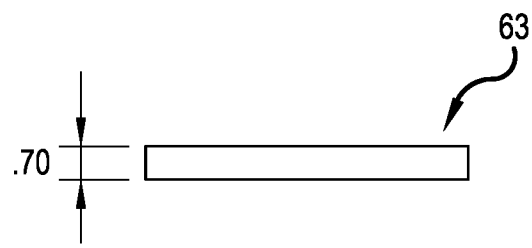
FIG. 24 is a side view of the metal ring of FIGS. 22 and 23.

Alternatively, the metal plate 95 may be press fitted against to the second lead 93 so that no gaps are present. The press fitting may be accomplished by punch riveting into place a metal ring 63, formed identical to the metal ring 63 used to secure the dielectric member 55 into the conductive outer shell 43. FIGS. 22, 23, and 24 are a perspective view, a top view and a side view, respectively, of one embodiment of the metal ring 63 used in the present invention. Illustrative dimensions in millimeters are given in FIGS. 23 and 24 to provide an example of the size of the metal ring 63, in one preferred embodiment of the present invention.

Because the conductive pin 73 passes through the central opening 85 in the feed-through capacitor 83, the conductive pin 73 cannot make electrical contact with the metal plate 95. Rather, the feed-through capacitor 83 creates a set capacitance between the conductive pin 73 and the conductive outer shell 43. Once assembled, the metal plate 95 resides between the second opening 47 of the conductive outer shell 43 and the feed-through capacitor 83.

The EMI filtering connector 41 of the present invention offers several advantages over the EMI filtering port of U.S. Pat. No. 7,632,122. Because the metal plate 95 is solid, no EMI can pass through it. The PCB 18 in the prior art of U.S. Pat. No. 7,632,122 included non-conductive materials 39a and 39b. EMI can freely pass through nonconductive materials 39a and 39b. Therefore, the metal plate 95 of the present invention should provide better EMI shielding.

Also, the feed-through capacitor 83 is located on the upstream signal side of the metal plate 95, with the upstream side being defined as the side of the metal plate not facing to the device to which the EMI filtering connector 41 is connected. Any EMI on the conductive pin 73 should be attenuated by the feed-through capacitor 83 before the conductive pin 73 passes to the downstream side of the metal plate 95. In the prior art of U.S. Pat. No. 7,632,122, the capacitors 20 are placed on the downstream side of the PCB 18. In other word, the leads of the capacitors 20, which convey the EMI on the conductive pin face directly at the device, and there is no shielding located between the capacitor leads and the circuitry within the device. Any EMI radiating away from the leads of the capacitors 20 could freely enter the device.

Also, the PCB 18, and the capacitors 20 and their leads are exposed to the elements of nature when the connector of U.S. Pat. No. 7,632,122 is not attached to a device. Often times, connectors are sold in sealed packages, e.g., plastic bags of ten or more units, such as one hundred connectors. Once the bag is opened to use one or more connectors, the technician stores the opened bag in a tool box or cabinet. If moisture is present, e.g., the tool box is carried in a vehicle or the cabinet is located in a warehouse, the moisture can lead to corrosion and damage to the PCB 18 and the capacitors 20 and their leads. The damage may result in altered performance characteristics and/or a failure to attenuate EMI.

Figure 21:
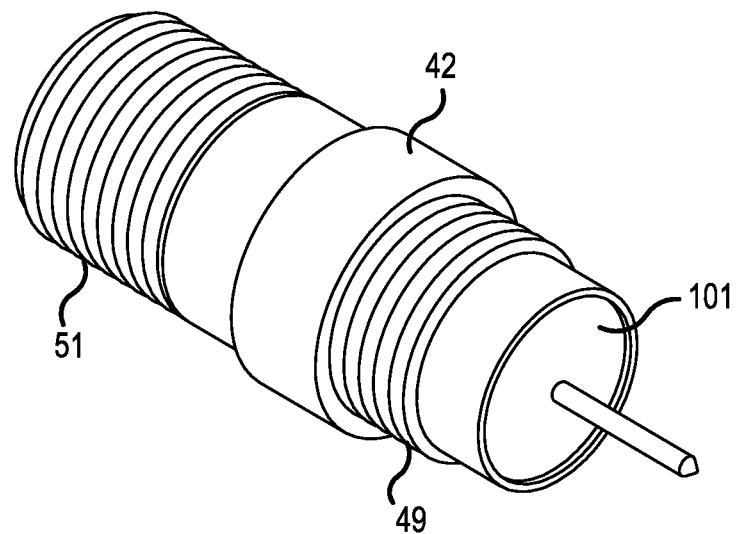
FIG. 21 is a front perspective view of a filler covering the feed-through capacitor to provide a moisture barrier.

The EMI filtering connector 41 of the present invention includes a moisture barrier, such as a filler 101, which completely seals the feed-through capacitor 83 and the metal plate 95 from the elements. As best seen in the perspective view of FIG. 21, the filler 101 resides on a downstream side of the conductive plate 95 opposite to the feed-through capacitor 83. The filler 101 seals the conductive plate 95 and feed-through capacitor 83 from an outside environment existing at the second opening 47. In one embodiment, the filler 101 is a glue or epoxy and completely fills the volume within the body 42 existing between the conductive plate 95 and an opening of body 42 facing to the second opening 47 of the conductive outer shell 43.

Although the EMI filtering connector 41 has thus far been illustrated as a separate inline device (having a female port at one end and a male port at the opposite end), the EMI filtering connector 41 may also be formed as an inline device with two female ports, or an inline device with two male ports. Also, the EMI filtering connector 41 may be formed as a power port connected to a device (having only a female port at a first end or a male port at the first end).

Figure 25:
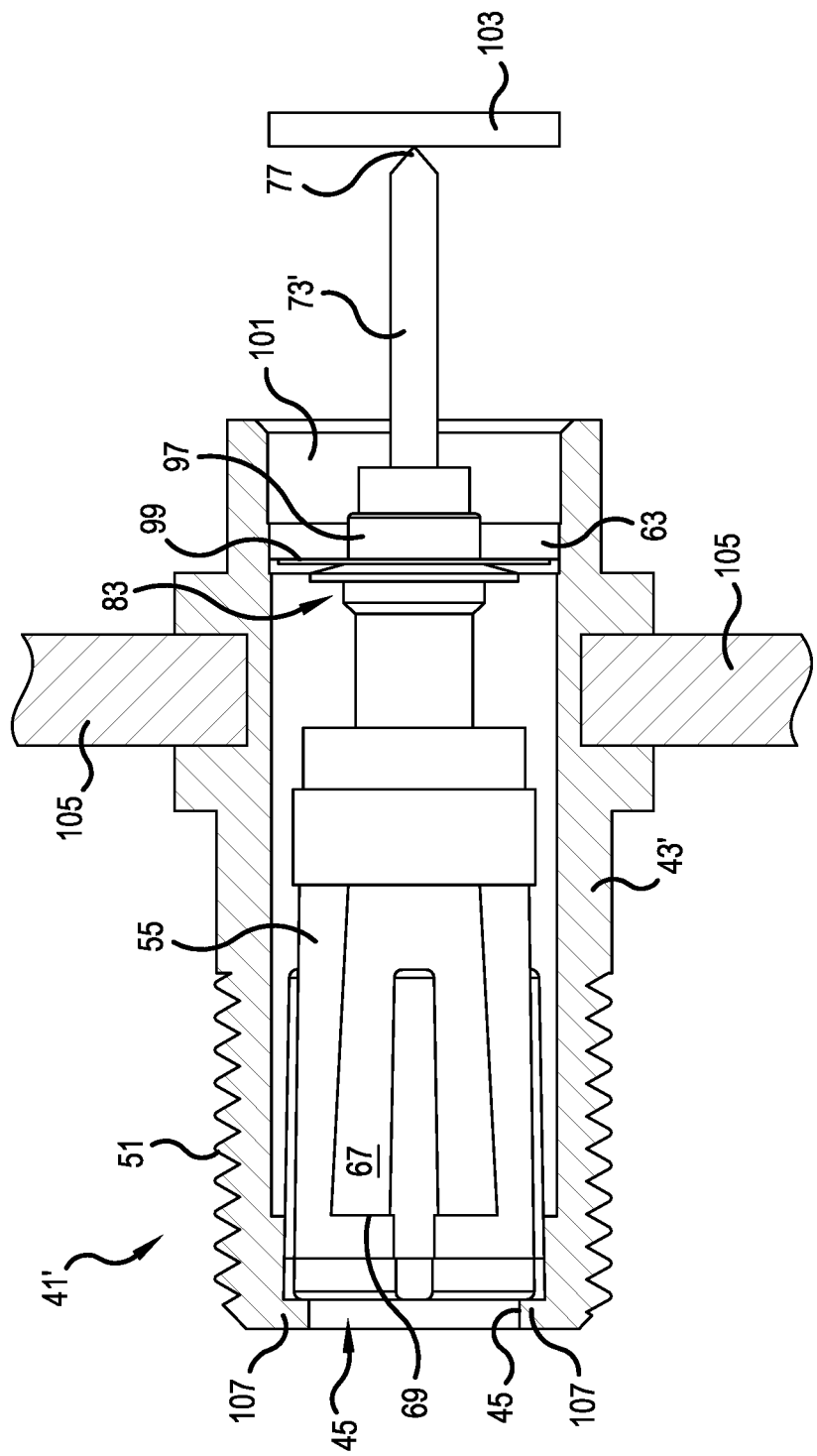
FIG. 25 is a side cut-away view of a modified, conductive outer shell showing a modified EMI filtering connector for use as a port on a device.

FIG. 25 is a side cut-away view of a modified, conductive outer shell 43' showing a modified EMI filtering connector 41'. The male cap 44 has been removed, as the connector 41' is now configured as a port. The conductive outer shell 43' captures a metal shielding wall 105 of the housing of the device having a power port formed by the modified EMI filtering connector 41'. Within the device is a printed circuit board (PCB) 103. The conductive pin 73' has an extended length, and the second end 77 of the conductive pin 73' is soldered to the PCB 103 to provide power to the device.

FIG. 25 also illustrates how the conductive outer shell 43' can have a closed lip 107 formed at the first opening 45 of the conductive outer shell 43'. The closed lip 107 prevents the dielectric member 55 from passing through the first opening 45, and hence replaces the need for a metal ring 63. In this embodiment, the dielectric member 55 is inserted into the second opening 47 during assembly, instead of the first opening 45.

Figure 26:
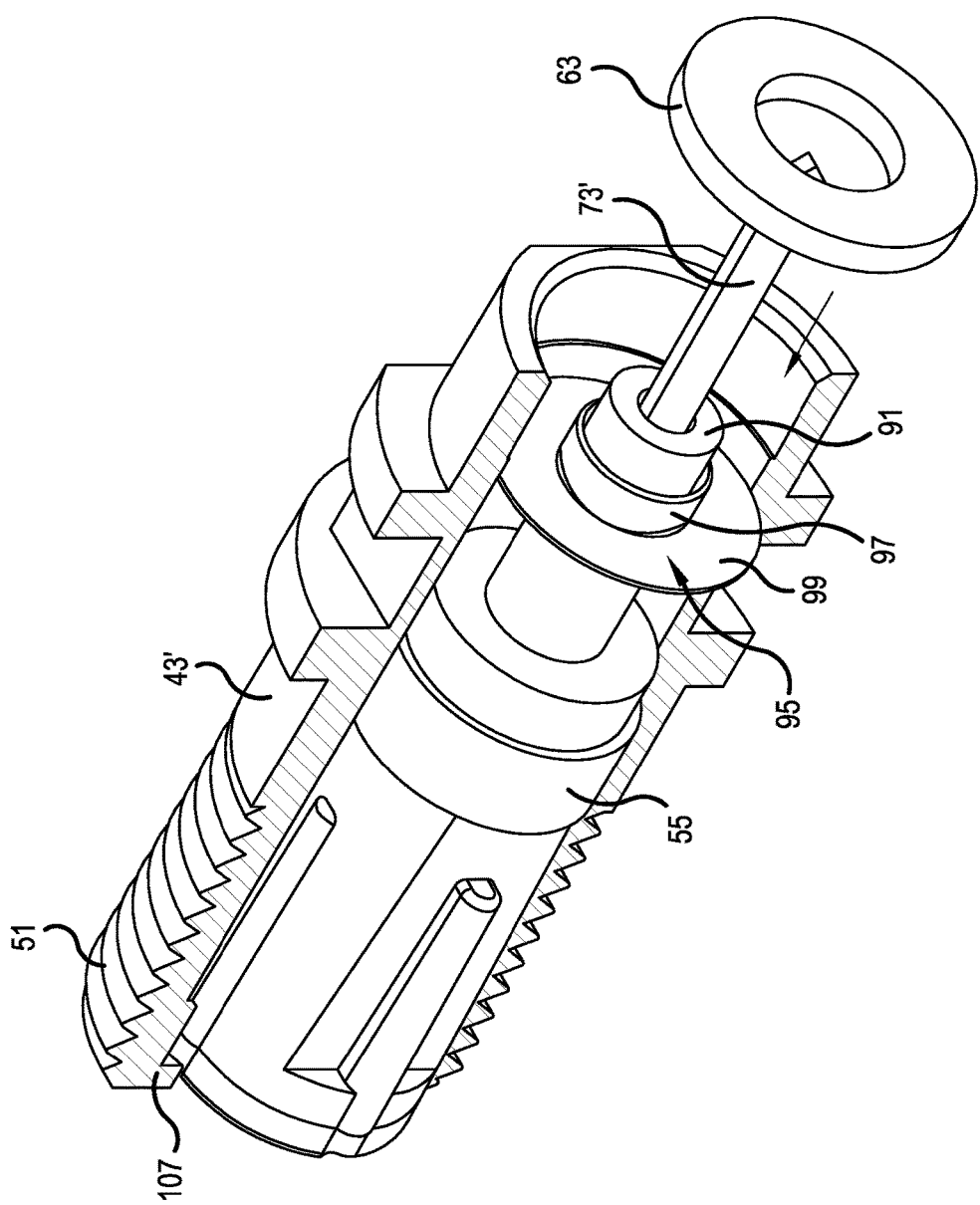
FIG. 26 is a perspective cut-away view of the conductive outer shell of FIG. 25, showing the metal ring prior to engagement with the conductive plate.

Although the conductive pin 73 has been shown as a separate member attached to the second end 71 of the pin receiving clamp 67 by solder 88, the conductive pin 73 may be integrally formed with the second end 71 of the pin receiving clamp 67. Further, the conductive pin 73 need not be round and may be a flat, planar member. FIG. 26 is a perspective cut-away view of the modified, conductive outer shell 43' showing the metal ring 63 prior to engagement with the conductive plate 95. FIG. 26 shows more details of the conductive outer shell 43', and the conductive pin 73' as a flat, planar member.

In a preferred embodiment, the conductive pin 73 is formed of a solid metal or alloy. However, it is within the scope of the present invention to form the conductive pin 73 with a hollow core, or to form the conductive pin of a non-conductive material coated or plated with a conductive material, e.g., a metal coating.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

The invention claimed is:

1. An EMI filtering coaxial power connector comprising:
   a conductive outer shell with a first opening and a second opening;
   a dielectric member disposed within said conductive outer shell;
   a conductive pin having a first end and a second end, said conductive pin being attached to said dielectric member; and
   a feed-through capacitor having a central opening and a first lead formed within said central opening, said conductive pin being electrically connected to said first lead, wherein a second lead of said feed-through capacitor is formed at an outer perimeter of said feed-through capacitor and is electrically connected to said conductive outer shell, wherein said conductive pin passes through said central opening of said feed-through capacitor, and wherein said second lead of said feed-through capacitor is formed entirely around said outer perimeter of said feed-through capacitor.

2. The connector of claim 1, wherein said conductive pin is soldered to said first lead of said feed-through capacitor.

3. The connector of claim 1, further comprising:
   a conductive plate mounted within said conductive outer shell, said conductive plate being disk-shaped with a central hole, an outer perimeter of said conductive plate being in electrical contact with said conductive outer shell and an inner perimeter of said central hole being in electrical contact with said second lead of said feed-through capacitor.

4. The connector of claim 3, wherein said outer perimeter of said conductive plate is press fitted to an inner portion of said conductive outer shell.

5. The connector of claim 3, wherein said inner perimeter of said central hole of said conductive plate is soldered to said second lead of said feed-through capacitor.

6. The connector of claim 5, wherein said outer perimeter of said conductive plate is soldered to an inner portion of said conductive outer shell.

7. The connector of claim 3, further comprising:
a filler residing on a side of said conductive plate opposite to said feed-through capacitor, said filler sealing said conductive plate from an outside environment existing at said second opening.

8. The connector of claim 7, wherein said filler is a glue or epoxy and completely fills the volume within a body of said conductive outer shell existing between said conductive plate and an opening of said body facing to said second opening of said conductive outer shell.

9. An EMI filtering coaxial power connector comprising:
a conductive outer shell with a first opening and a second opening;
a dielectric member disposed within said conductive outer shell;
a conductive pin having a first end and a second end, said conductive pin being attached to said dielectric member;
at least one capacitor mounted within said conductive outer shell, said at least one capacitor having a first lead electrically connected to said conductive pin and a second lead electrically connected to said conductive outer shell;
a metal plate mounted within said conductive outer shell, said metal plate having a central hole, an outer perimeter of said metal plate being in electrical contact with said conductive outer shell, said conductive pin passing through said central hole without making electrical contact with said metal plate, wherein said metal plate resides between said second opening of said conductive outer shell and said at least one capacitor; and
a pin receiving clamp located within said conductive outer shell, wherein said pin receiving clamp is directly attached to said dielectric member and includes a second end attached to, and electrically connected to, said first end of said conductive pin, and wherein said pin clamp includes a first end located proximate said first opening of said conductive outer shell and being dimensioned to receive another pin of a male coaxial connector mated to said first opening of said conductive outer shell, wherein said second end of said pin extends to a point proximate said second opening of said conductive outer shell and acts in conjunction with inner threads formed proximate said second opening of said conductive outer shell to form a male coaxial connector.

10. The connector of claim 9, further comprising:
a filler residing on a side of said metal plate opposite to said at least one capacitor, said filler sealing said metal plate from an outside environment existing at said second opening.

11. The connector of claim 10, wherein said filler is a glue or epoxy and completely fills the volume within a body of said conductive outer shell existing between said metal plate and an opening of said body facing to said second opening of said conductive outer shell.

12. An EMI filtering coaxial power connector comprising:
a conductive outer shell with a first opening and a second opening;
a dielectric member disposed within said conductive outer shell;
a conductive pin having a first end and a second end, said conductive pin being attached to said dielectric member;
at least one capacitor mounted within said conductive outer shell, said at least one capacitor having a first lead electrically connected to said conductive pin and a second lead electrically connected to said conductive outer shell;
a metal plate mounted within said conductive outer shell, said metal plate having a central hole, an outer perimeter of said metal plate being in electrical contact with said conductive outer shell, said conductive pin passing through said central hole without making electrical contact with said metal plate, wherein said metal plate resides between said second opening of said conductive outer shell and said at least one capacitor; and
a pin receiving clamp located within said conductive outer shell, wherein said pin receiving clamp is directly attached to said dielectric member and includes a second end attached to, and electrically connected to, said first end of said conductive pin, and wherein said pin clamp includes a first end located proximate said first opening of said conductive outer shell and being dimensioned to receive another pin of a male coaxial connector mated to said first opening of said conductive outer shell, wherein an outer surface of said first opening of said conductive outer shell includes threads for engaging a male coaxial connector.

13. The connector of claim 12, wherein said second end of said pin extends out of said second opening of said conductive outer shell for attachment to a printed circuit board and acts in conjunction with said conductive outer shell to form a power port for a device.

14. The connector of claim 12, wherein said second end of said pin extends to a point proximate said second opening of said conductive outer shell and acts in conjunction with inner threads formed proximate said second opening of said conductive outer shell to form a male coaxial connector.

15. The connector of claim 14, wherein said at least one capacitor is a feed-through capacitor having a central opening and wherein said first lead is formed within said central opening and said second lead is formed at an outer perimeter of said feed-through capacitor.

16. The connector of claim 15, wherein said conductive pin passes through said central opening of said feed-through capacitor and wherein said second lead of said feed-through capacitor is formed entirely around said outer perimeter of said feed-through capacitor and is electrically connected to said conductive outer shell via said metal plate.

17. The connector of claim 14, wherein said metal plate is a solid brass plate.

18. The connector of claim 14, further comprising:
a solder joint connecting said outer perimeter of said metal plate with an inner ledge of said conductive outer shell.

19. The connector of claim 14, further comprising:
a filler residing on a side of said metal plate opposite to said at least one capacitor, said filler sealing said metal plate from an outside environment existing at said second opening.

20. The connector of claim 19, wherein said filler is a glue or epoxy and completely fills the volume within a body of said conductive outer shell existing between said metal plate and an opening of said body facing to said second opening of said conductive outer shell.

\* \* \* \* \*